United States Patent
Seguin et al.

(10) Patent No.: US 6,280,715 B1
(45) Date of Patent: Aug. 28, 2001

(54) COSMETIC COMPOSITION USEFUL NOTABLY FOR THE SKIN WHITENING AND MELANOGENESIS INHIBITING AGENT CONTAINING SUCH A COSMETIC COMPOSITION

(75) Inventors: Marie-Christine Seguin, Monaco (MC); Mark A. Babizhayev, Ivanovskaya 20, 74, 127434, Moscow (RU)

(73) Assignees: Exsymol S.A.M. (MC); Mark A. Babizhayev, Moscow (RU)

( * ) Notice: Subject to any disclaimer, the term of this patent is extended or adjusted under 35 U.S.C. 154(b) by 0 days.

(21) Appl. No.: 09/126,322

(22) Filed: Jul. 31, 1998

(30) Foreign Application Priority Data

Jul. 31, 1997 (MC) ........................................ 2383

(51) Int. Cl.⁷ ............................ A61K 7/02; A61K 31/66; A61K 31/695
(52) U.S. Cl. ........................... 424/69; 424/600; 424/601; 514/63; 514/75; 514/80; 514/95
(58) Field of Search ............................ 424/69, 600, 601; 514/80, 844, 63, 75, 95

(56) References Cited

U.S. PATENT DOCUMENTS

| | | | | |
|---|---|---|---|---|
| 4,072,742 | * | 2/1978 | Bouillon et al. | 424/47 |
| 4,205,977 | * | 6/1980 | Dingwall et al. | 71/76 |
| 5,194,262 | * | 3/1993 | Goldberg et al. | 424/401 |
| 5,264,207 | * | 11/1993 | Bommelear et al. | 424/69 |
| 5,476,847 | * | 12/1995 | McKittrick et al. | 514/80 |
| 5,972,319 | * | 10/1999 | Linn et al. | 424/65 |

\* cited by examiner

*Primary Examiner*—Christopher S. F. Low
*Assistant Examiner*—Anish Gupta
(74) *Attorney, Agent, or Firm*—James C. Lydon

(57) ABSTRACT

Cosmetic composition useful notably in the whitening of skin which it includes, in association with any suitable excipient, at least one compound of the following general formula (I):

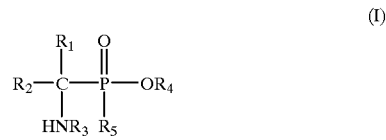

wherein:
- $R_1$ represents a hydrogen atom, a linear or branched alkyl group or a thiazoline group,
- $R_2$ represents a hydrogen atom, a linear or branched alkyl group or a linear or branched alkyl group substituted by a carboxyl, a hydroxyl, an amine or a thiol group,
- $R_3$ represents a hydrogen atom, a linear or branched alkyl group, an arylalkyl group, an acyl group or an acyloxy group,
- $R_4$ represents a hydrogen atom or a linear or branched alkyl group,
- $R_5$ represents a hydrogen atom, a hydroxyl group or a linear or branched alkyl group.

16 Claims, No Drawings

COSMETIC COMPOSITION USEFUL NOTABLY FOR THE SKIN WHITENING AND MELANOGENESIS INHIBITING AGENT CONTAINING SUCH A COSMETIC COMPOSITION

FIELD OF THE INVENTION

The present invention relates to a cosmetic composition notably useful for the skin whitening, containing a compound of the general formula (I) as described hereafter, in association with any suitable excipient, the present invention relates also to a melanogenesis inhibiting agent containing such a cosmetic composition.

The compounds (I) according to the invention have the general formula:

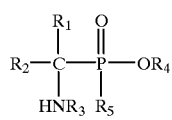

(I)

wherein $R_1$ represents a hydrogen atom, a linear or branched alkyl group or a thiazoline group, $R_2$ represents a hydrogen atom, a linear or branched alkyl group or a linear or branched alkyl group substituted by a carboxyl, a hydroxyl, an amine or a thiol group, $R_3$ represents a hydrogen atom, a linear or branched alkyl group, an arylalkyl group, an acyl group or an acyloxy group, $R_4$ represents a hydrogen atom or a linear or branched alkyl group, $R_5$ represents a hydrogen atom or a hydroxyl group or a linear or branched alkyl group.

BACKGROUND OF THE INVENTION

For several years, there has been a growing interest, in the field of cosmetics, for depigmenting products: age spots (lentigo senile), chloasma, freckles, pigmentation spots that appear on mature skins after a prolonged exposure to the sun, are badly tolerated by affected people.

Fashion phenomena favouring light complexions in Asia and Africa are also factors in favour of the development of depigmenting products.

Melanin is a pigment synthesized by melanocytes which are specific cells of the epidermal basal layer.

Hyperpigmentations are often caused by hyperactivity of the melanocytes, eventually associated to an increase of their number.

Within melanocytes, oxidation reactions that lead to the formation of melanin are mainly catalyzed by tyrosinase. Resulting pigments are uniformly distributed over the epidermis surface, except when the mechanism is disrupted: melanin is then anarchically accumulated in some areas.

The depigmenting properties of some substances have been known for long: as soon as 1936, Oettel noticed a decrease of pigmentation among black cats hair which had been given hydroquinone (Hemsworth B. N., J.Soc Cosmet. Chem., 1973, 24, 727–733).

Some substances showed a depigmenting action but cannot be used in cosmetic because of their toxicity (for example, mercury salts), of the cutaneous irritation they induce (mercaptoamines, oxidizing products such as hydrogen peroxide) or because of the excessive slowness of their action (ascorbic acid or ascorbic acid derivatives).

Other compounds such as phenolic derivatives, corticosteroids, analogs of vitamin A, some vegetal extracts are used as components in many depigmenting preparations now on the market.

However, these compounds show some side-effects: among phenolic derivatives, hydroquinone, which is an inhibitor of tyrosinase, induces quite a few secondary reactions (inflammatory reactions, burns, prickling sensations, irreversible dyschromia in spots); corticosteroids induce such secondary reactions and cannot be used in cosmetic; analogs of vitamin A (beta carotene, canthaxanthine) are able to block the melanocyte activity but the problem with these substances is making them to penetrate into the cells without being metabolized by the cell enzymes. Plant extracts, containing either arbutin (glucose hydroquinone) or flavonoids or also cinnamic derivatives, are also used as depigmenting agents but have a very slow action.

Generally speaking, the problem with these depigmenting agents of the prior art is that it will take at least a two months treatment before seeing the first results in vivo.

SUMMARY OF THE INVENTION

To notably remedy these drawbacks, one purpose of the present invention is to suggest the use, for skin whitening, of compounds whose structure and manufacturing process are known, but have a surprising effect in skin whitening.

One purpose of the present invention is to propose a cosmetic composition useful notably in the skin whitening, characterized in that it contains, in association with any suitable excipient, at least one compound of the following general formula (I):

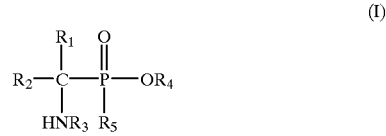

(I)

wherein $R_1$ represents a hydrogen atom, a linear or branched alkyl group or a thiazoline group, $R_2$ represents a hydrogen atom, a linear or branched alkyl group or a linear or branched alkyl group substituted by a carboxyl, a hydroxyl, an amine or a thiol group, $R_3$ represents a hydrogen atom, a linear or branched alkyl group, an arylalkyl group, an acyl group or an acyloxy group, $R_4$ represents a hydrogen atom or a linear or branched alkyl group, $R_5$ represents a hydrogen atom, a hydroxyl group or a linear or branched alkyl group.

DETAILED DESCRIPTION OF THE PREFERRED EMBODIMENTS

Preferably, the compound of formula (I) is such as $R_1$ represents a hydrogen atom, a ($C_1$–$C_4$) alkyl group or a thiazoline group, $R_2$ and $R_3$ represent each one a hydrogen atom, and $R_5$ represents a hydrogen atom or a hydroxyl group.

Advantageously, the compound of formula (I) is such as $R_1$ represents a ($C_1$–$C_4$) alkyl group, $R_2$ and $R_3$ represent each one a hydrogen atom, and $R_5$ represents a hydrogen atom.

According to a preferred embodiment, the compound of formula (I) is the 1-amino-ethylphosphinic acid.

According to another preferred embodiment of the invention, the compound of formula (I) is the 1-amino-3-methylbutylphosphinic acid.

Preferably, the cosmetic composition according to the invention contains, in addition to compounds of general formula (I), anti-inflammatory agents, other skin whitening agents and/or antioxidants.

Advantageously, the content of compound of general formula (I) is included between 0.1 and 20% in weight in relation to the total weight of the composition and preferably between 0.5 and 5% in weight in relation with the total weight of the composition.

According to a special embodiment, the composition according to the invention contains in addition an organo-silicon compound of the following general formula:

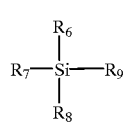

(II)

wherein:
at least one of the radicals $R_6$, $R_7$, $R_8$ or $R_9$ represents a hydroxyl group or an alkoxy, acyloxy, aryloxy or amine group, or a halogen atom, and at least one other of said radicals $R_6$, $R_7$, $R_8$ or $R_9$ represents an alkyl group.

According to a special embodiment of the invention, the cosmetic composition contains in addition a pseudo-dipeptide such as one of the type obtained by the coupling between histamine and an aminoacid.

Preferably, this pseudo-dipeptide is the β-alanyl-histamine.

Preferably, the excipient used in the cosmetic composition according to the invention, is a micro-dispersion without surfactant.

Advantageously, the cosmetic composition according to the invention is in the form of liposomes, microparticles or nanoparticles.

According to an advantageous alternative of the invention, the cosmetic composition is in the form of a cream, a milk, a lotion, or a gel.

Another purpose of the invention is to propose a melanogenesis inhibiting agent, characterized in that it contains a cosmetic composition as described above.

The present invention will be better understood through the following description and examples, which illustrate the invention in a non restrictive way.

The compounds of general formula (I) are commercially available or can be prepared according to the methods described in the prior art, notably according to the procedure described in J. Chem. Perkin. trans. I, 1984 by BAYLIS and al.

The compounds of formula (I) preferred are those in which $R_1$ represents a hydrogen atom, a ($C_1$–$C_4$) alkyl group or a thiazoline group, $R_2$ and $R_3$ represent each one a hydrogen atom, and $R_5$ represents a hydrogen atom or a hydroxyl group.

Among these compounds, aminophosphinic acids, that is to say compounds of formula (I) in which $R_5$ represents a hydrogen atom are particularly preferred.

The compounds according to the invention are alpha-amino phosphonic or alpha-amino phosphinic acids and have thus a structure close to the structure of a natural alpha-amino acid.

The compounds used for compositions according to the invention have in themselves an inhibiting action on melanogenesis.

The mechanisms of this action are not precisely known, and it is possible that the observed activity is the consequence of several mechanisms working simultaneously and eventually in a synergetic way.

Thus, compounds according to the invention can be useful for skin whitening because they inhibit tyrosinase, and/or because they act at other levels.

According to a preferred embodiment of the invention, in the cosmetic compositions according to the invention, at least one other compound useful for the skin whitening is added to the compound of general formula (I).

Advantageously, the other compound(s) useful in the skin whitening contain at least one inhibitor of tyrosinase.

Preferably, said other compound(s) effective in the skin whitening are ascorbic acid and/or its derivatives; particularly its stearate or palmitate salts or the ascorbic acid combined with a stabilizer, such as notably the compound known on the market under the trademark ASCORBOSILANE C® and marketed by the Applicant.

Said other compound(s) useful in the skin whitening can also be kojic acid or its derivatives.

According to an advantageous alternative of the invention, said other compound(s) useful for the skin whitening are natural plant extracts, and more particularly the extract of white mulberry (*Morus alba*), green tea (*Thea sinensis*), matriarca (*Chamomilla recutica*) Green tea is known for its properties of inhibiting the transfer of mature melanocytes to keratinocytes. It is also an inhibitor of tyrosinase. Matriarca is an endotheline agonist, that inhibits melanogenesis induced by UV irradiation.

According to an other special embodiment of the invention, at least one anti-inflammatory agent is added in cosmetic compositions according to the invention, notably substances with a soothing action. Advantageously, this anti-inflammatory agent has a natural origin. It is preferably licorice phytosterol.

It is known, for example, that some dyschromia, such as age spots, appears with ageing. The inventors have noticed that when fighting the ageing process, notably with anti-ageing cosmetic compositions, skin marks connected with ageing decrease and, particularly, the apparition of age spots is prevented.

Thus, according to a first special embodiment of the invention, the compound of general formula (I) is associated to a cosmetic active known for its anti-ageing action.

Preferably, the anti-ageing cosmetic active is an organo-silicon compound, biologically active, like the silanols marketed by the Applicant.

Advantageously, this organo-silicon compound corresponds to the following general formula (II):

(II)

wherein:
one at least of the $R_6$, $R_7$, $R_8$ or $R_9$ radicals represents a hydroxyl group or a hydrolyzable group containing at least one oxygen atom in such a way there is a Si—O bond and at least one other of said radicals $R_6$, $R_7$, $R_8$ or $R_9$ represents an alkyl group.

In addition, it has been shown that glycation phenomena, lipid peroxidation and oxidative stress situations can cause the appearance of an excessive pigmentation of the skin.

For instance, it is shown that the synthesis of a compound like lipofuscin, an aldehyde-derivatives polymer known to be an age pigment, is regulated by pro and anti-oxidation reactions.

This is the reason why, according to a special embodiment, the cosmetic compositions according to the invention are carried out by adding at least one compound of general formula (I) with at least one antioxidant.

Besides, it is known that DNA destruction and/or its repair induces melanization.

According to a second special embodiment of the invention, the cosmetic composition contains, in addition to the compound of formula (I) and eventually but not necessarily an organo-silicon compound, a compound particularly known for its DNA protecting and/or repairing properties.

Preferably, this DNA protecting compound is a pseudo-dipeptide of one of the type obtained in combining histamine to an amino acid as detailed in the application for international patent WO94/19325.

This pseudo-dipeptide is preferably the β-alanyl-histamine, also known for its anti-oxidative properties and for its ability to reduce fatty acids hydroperoxides.

The proportions of the compound of general formula (I) in the compositions according to the invention depend of the ingredients used in these compositions and can vary from 0.1% to 20% in weight. Nevertheless, the preferred proportions vary between 0.5% and 5% in weight.

In all cosmetic compositions according to the invention, the excipient can be any excipient suitable in the field of cosmetics. Advantageously, the excipient is a micro-dispersion with no surfactant.

According to a special embodiment of the invention, the cosmetic compositions according to the invention are under the form of liposomes, microparticles or nanoparticles.

Cosmetic compositions according to the invention can also be in any form cosmetically suitable, and notably in any form suitable for topical use such as cream, milk, lotion or gel.

The invention relates also to a melanogenesis inhibiting agent containing one of the cosmetic compositions described above.

The following examples illustrate, in a non restrictive way, the inhibiting action on melanin of the compounds of formula (I) used for compositions according to the invention:

EXAMPLE 1

The inhibiting activity on melanin of the 1-amino-ethylphosphinic acid of the following developed formula (Ia) is tested, in vitro:

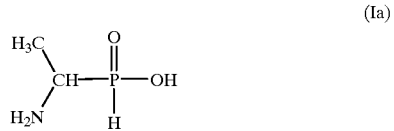

(Ia)

The reference used is the ascorbic acid in solution at $0.3.10^{-3}$ mole $l^{-1}$.

2 ml of a L-DOPA solution, 1.25 ml of tyrosinase (2500 units/ml), 2 ml of product (Ia) diluted at $1.10^{-3}$ mole.$l^{-1}$ are mixed together, and the mixture is completed with 20 ml of phosphate buffer ($NaH_2PO_4$ 0.1 mole $l^{-1}$+$Na_2HPO_4$ 0.1 mole.$l^{-1}$, pH=6.8). The mixture is stirred for 4 hours at 37° C., then allowed to cool at room temperature for one night, shielded from light.

1 ml of concentrated hydrochloric acid is added and the mixture is centrifuged at 4000 rpm for 5 min. The pellet is washed with 10 ml of distilled water then centrifuged a second time. A reflux is made on the pellet with concentrated acid HCL 6N for 48 hours. The dried pellet is dissolved in 10 ml of toluene, exposed to ultrasounds for 2 min, put 2 hours at 37° C. then exposed to ultrasounds again for 5 min. The optical density is measured at 400 nm.

The percentage of inhibition of melanin by the 1-amino-ethylphosphinic acid is 46%.

EXAMPLE 2

The inhibiting activity on melanin of the 1-amino-3-methylbutylphosphinic acid, of the following developed formula (Ib):

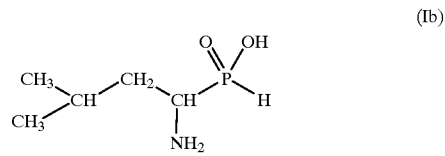

(Ib)

is tested in vitro using the procedure of example 1.

The percentage of inhibition of melanin by the 1-amino-3-methylbutylphosphinic acid is 44%.

EXAMPLE 3

The inhibiting activity on melanin, of the 1-amino-ethylphosphinic acid (Ia) is studied on S91 melanoma cells cultures.

The model of study was finalized by Gilchrest (1987).

The cultured cells are purchased from a Cloudman melanom.

As ordinary melanocytes, they respond to UV stimuli by an increase of melanogenesis.

The melanogenesis evaluation is made through the melanin content and the activity of enzymes involved in this metabolism: tyrosinase and dopa-tautomerase.

S91 cells are plated in P60 dishes at a density of $2.10^{-5}$ cells per dish and maintained in Dubelcco's modified Eagle's medium and provided with 10% of calf serum. When the cells have reached about 50% of confluence, they are exposed to a UV irradiation of 10 mJ/cm² at 285±5 nm. During irradiation, the medium is replaced with a salin phosphate solution (PBS) to eliminate the forming of toxical derivatives. Immediately after irradiation, the PBS is replaced with fresh medium/7% of calf serum with or without the active agent. After a 16 hours incubation, the medium is replaced with ordinary medium with or without the active agent.

Evaluation of the result is done 24 or 48 hours after irradiation. The control culture, which have not been irradiated, is subjected to the same process but left in dark during irradiation.

The melanin content is then determined: melanocytes are trypsinized, twice washed with PBS and dissolved in 0.8 ml of NaOH 1N, when strongly vortexed for 10–15 min and heated at 60–80° C. The melanin concentration is determined based on the absorbance at 475 nm.

The reference, kojic acid, is used at a concentration of $3.3.10^{-3}$ mole.$l^{-1}$; at such concentration, it decreases the melanin content of 45.2%.

The (Ia) compound, at a concentration of $0.5.10^{-3}$ mole.$l^{-1}$, that is much less concentrated than the reference, produces a 47.2% decrease of melanin rate in the cells.

EXAMPLE 4
Microdispersion Oil in Water Without Surfactant.

| | |
|---|---|
| Hydrogenated polyisobutene | 10.75 g |
| mineral oil | 3.00 g |
| stearyl heptanoate | 7.25 g |
| sodium methyl parahydroxybenzoate | 0.20 g |
| propyl parahydroxybenzoate | 0.10 g |
| 1-amino-ethylphosphinic acid | 1.00 g |
| ALISTIN (7-02 & 6-20) | 0.20 g |
| carbomer | 0.50 g |
| water | 79.00 g |

EXAMPLE 5
Gel

| | |
|---|---|
| Carbomer | 0.70 g |
| sodium methyl parahydroxybenzoate | 0.20 g |
| propyl parahydroxybenzoate | 0.10 g |
| 1-amino-ethylphosphinic acid | 2.00 g |
| Mulberry extract | 3.00 g |
| Water | 94.00 g |

EXAMPLE 6
Cream

| | |
|---|---|
| polyacrylamide | 2.00 g |
| $C_{13-14}$ isoparaffin | 2.00 g |
| Laureth 7 | 2.00 g |
| Imidazolidinyl urea | 0.30 g |
| sodium methyl parahydroxybenzoate | 0.10 g |
| propyl parahydroxylbenzoate | 0.05 g |
| 1-amino-ethylphosphinic acid | 3.00 g |
| glyceryl stearate | 10.00 g |
| steareth-25 | 10.00 g |
| cetheth-20 | 10.00 g |
| stearic alcohol | 10.00 g |
| Cetearyl octanoate | 10.00 g |
| macadamia oil | 10.00 g |
| dimethicone | 0.20 g |
| dimethicone copolyol | 0.30 q |
| glycerin | 3.00 g |
| water | q.s.p. 100.00 g |

What is claimed is:

1. A cosmetic composition useful notably in the whitening of skin, comprising in association with any cosmetically acceptable excipient, at least one compound of the following general formula (I):

$$\begin{array}{c} R_1 \quad O \\ | \quad \| \\ R_2-C-P-OR_4 \\ | \quad | \\ HNR_3 \; R_5 \end{array} \quad (I)$$

wherein:
$R_1$ represents a hydrogen atom, a linear or branched alkyl group or a thiazoline group,
$R_2$ represents a hydrogen atom, a linear or branched alkyl group or a linear or branched alkyl group substituted by a carboxyl, a hydroxyl, an amine or a thiol group,
$R_3$ represents a hydrogen atom, a linear or branched alkyl group, an aralkyl group, an acyl group or an acyloxy group,
$R_4$ represents a hydrogen atom or a linear or branched alkyl group,
$R_5$ represents a hydrogen atom, a hydroxyl group or a linear or branched alkyl group; wherein the composition additionally contains an organosilicon compound of the following general formula (II):

$$\begin{array}{c} R_6 \\ | \\ R_7-Si-R_9 \\ | \\ R_8 \end{array} \quad (II)$$

wherein at least one of the radicals $R_6$, $R_7$, $R_8$, or $R_9$ represents a hydroxyl group or an alkoxy, acyloxy, aryloxy, or amine group, or a halogen atom and at least another of said radicals $R_6$, $R_7$, $R_8$, or $R_9$ represents an alkyl group.

2. Cosmetic composition according to claim 1 wherein it contains in addition to a pseudo-dipeptide obtained by the coupling between histamine and an aminoacid.

3. Cosmetic composition according to the claim 2, wherein said pseudo-dipeptide is the β-alanyl-histamine.

4. A method for whitening an individual's skin, comprising applying a cosmetic composition to said skin for a time sufficient to whiten said skin, wherein said composition comprises any cosmetically acceptable excipient in combination with at least one compound of the following general formula (I):

$$\begin{array}{c} R_1 \quad O \\ | \quad \| \\ R_2-C-P-OR_4 \\ | \quad | \\ HNR_3 \; R_5 \end{array} \quad (I)$$

wherein:
$R_1$ represents a hydrogen atom, a linear or branched alkyl group or a thiazoline group,
$R_2$ represents a hydrogen atom, a linear or branched alkyl group or a linear or branched alkyl group substituted by a carboxyl, a hydroxyl, an amine or a thiol group,
$R_3$ represents a hydrogen atom, a linear or branched alkyl group, an aralkyl group, an acyl group or an acyloxy group,
$R_4$ represents a hydrogen atom or a linear or branched alkyl group,
$R_5$ represents a hydrogen atom, a hydroxyl group or a linear or branched alkyl group.

5. The method of claim 4, wherein said compound is 1-amino-ethylphosphinic acid.

6. The method of claim 4, wherein said compound is 1-amino-3-methylbutylphosphinic acid.

7. The method of claim 4, wherein said composition contains from 0.1 to 20 weight percent of said compound, based on the total weight of the composition.

8. The method of claim 4, wherein said composition further contains an organosilicon compound of the following general formula (II):

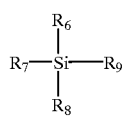

(II)

wherein at least one of the radicals $R_6$, $R_7$, $R_8$, or $R_9$ represents a hydroxyl group or an alkoxy, aryloxy, or amine group, or a halogen atom and at least another of said radicals $R_6$, $R_7$, $R_8$, or $R_9$ represents an alkyl group.

9. The method of claim 4, wherein $R_1$ represents a hydrogen atom, a ($C_1$–$C_4$) alkyl group or a thiazoline group, $R_2$ and $R_3$ individually represent a hydrogen atom, and $R_5$ represents a hydrogen atom or a hydroxyl group.

10. The method of claim 4, wherein $R_1$ represents a ($C_1$–$C_4$) alkyl group, $R_2$ and $R_3$ individually represent a hydrogen atom, and $R_5$ represents a hydrogen atom.

11. The method of claim 4, wherein said cosmetic composition further comprises at least one additional component selected from the group consisting of an anti-inflammatory agent, another skin whitening agent, and an antioxidant.

12. The method of claim 4, wherein the content of the compound of general formula (I) is present in an amount ranging between 0.5 and 5 weight percent based on the total weight of the composition.

13. The method of claim 4, wherein said composition further comprises a pseudo-dipeptide obtained by the coupling between histamine and an amino acid.

14. The method of claim 4, wherein said excipient comprises a micro-dispersion in the absence of a surfactant.

15. The method of claim 4, wherein said composition is in the form of liposomes, microparticles or nanoparticles.

16. The method of claim 4, wherein said composition is in the form of a cream, a milk, a lotion or a gel.

* * * * *